United States Patent
Nakhjavan

[19]

[11] Patent Number: 5,772,674
[45] Date of Patent: Jun. 30, 1998

[54] CATHETER FOR REMOVAL OF CLOTS IN BLOOD VESSELS

[76] Inventor: Fred K. Nakhjavan, 914 Morgan Rd., Rydal, Pa. 19046

[21] Appl. No.: 829,381

[22] Filed: Mar. 31, 1997

[51] Int. Cl.$^6$ .................................................. A61B 17/22
[52] U.S. Cl. ........................... 606/159; 606/194; 604/96; 604/53
[58] Field of Search ....................... 604/53, 96; 606/101, 606/159, 170, 127, 200, 194

[56] References Cited

U.S. PATENT DOCUMENTS

| | | | |
|---|---|---|---|
| 4,794,928 | 1/1989 | Kletschka | 606/194 |
| 4,911,163 | 3/1990 | Fina | 606/127 |
| 5,011,488 | 4/1991 | Ginsburg | 606/159 |
| 5,092,839 | 3/1992 | Kipperman | 604/53 |
| 5,102,415 | 4/1992 | Guenther et al. | 606/159 |
| 5,192,268 | 3/1993 | Shiber | 604/53 |
| 5,366,463 | 11/1994 | Ryan | 606/159 |

*Primary Examiner*—Michael Buiz
*Assistant Examiner*—David O. Reip
*Attorney, Agent, or Firm*—William H. Eilberg

[57] ABSTRACT

A thrombectomy catheter includes a delivery catheter and a receiving catheter, both having balloons at their distal ends. The balloons are made of a material which, when inflated, assumes the shape of a receptacle. The thrombectomy catheter is inserted, as a unit, into a vessel, and advanced to the vicinity of a clot. Then, the delivery catheter is advanced, while the receiving catheter remains fixed, until the balloons of the two catheters are disposed on opposite sides of the clot. The balloons are inflated to occupy substantially the entire cross-section of the vessel, and the delivery catheter is withdrawn, causing its balloon to draw the clot into the receiving catheter. The clot therefore becomes encased between the balloons. The balloons are partially deflated, and the catheters are withdrawn as a unit, bringing with them the encased clot material.

17 Claims, 5 Drawing Sheets

CATHETER FOR REMOVAL OF CLOTS IN BLOOD VESSELS

BACKGROUND OF THE INVENTION

This invention relates to the field of interventional cardiology or radiology, and provides a method and device for removing clots from blood vessels, especially coronary arteries.

Various devices and techniques have been proposed for removing clots from blood vessels, especially coronary vessels. These include transluminal extraction catheters (TEC), directional coronary atherectomy (DCA), laser catheters, and rheolytic catheters.

The TEC device is a large catheter which is difficult to maneuver to distal parts of vessels, and often requires additional use of other devices, such as adjunctive balloon angioplasty or stents.

A directional coronary atherectomy catheter (known as an "atherocath") is also a large device which is not specific for removal of clots. In fact, by advancing the atherocath into the thrombus-containing lesions, embolization may occur.

Rheolytic catheters are investigational devices, and the equipment is very expensive. Laser catheters for removal of clots are also investigational devices.

One proposed solution to the problem of removing a blood clot from a blood vessel is described in U.S. Pat. No. 5,092,839. The latter patent shows a thrombectomy catheter, with a balloon catheter inserted inside it, the thrombectomy catheter being threaded through a vessel to a position just short of the clot. The balloon is inflated, thereby expanding the distal end of the thrombectomy catheter, and forming that end into a receptacle. Then, the balloon is deflated, and the balloon catheter can be advanced such that the balloon is located at a position beyond the clot. The balloon is then inflated again. When the balloon catheter is withdrawn, the clot material is pulled into the receptacle formed by the expanded distal end of the thrombectomy catheter.

The technique shown in the above-cited patent has two main disadvantages. First, it does not have the maneuverability of the balloon catheters, because of its large size. This is of particular importance in smaller vessels, i.e. tortuous vessels or smaller side branches. Secondly, since the clot may not be removed completely in one approach, and since a thrombectomy catheter is irreversibly expanded, if a second or third approach is necessary, then a new catheter must be used for each additional treatment.

Since expanding the catheter stops the blood flow, causing ischemia, the procedure must be done speedily to prevent the consequences of ischemia, i.e. heart attack or life-threatening arrhythmias. By contrast, with the present invention, the balloon can be deflated so that blood flow is established. After the balloon has returned to its previous state, it can be inflated again for another approach to remove the clot.

Another prior art technique is described in U.S. Pat. No. 5,011,488. In the latter patent, a blood clot is sandwiched between an inflated balloon and a spring-loaded flexible conical tip. The latter technique has the same disadvantages discussed above. When the conical tip is not constrained by the tube in which it normally sits, the tip expands, due to a spring force, to a configuration of maximum diameter. Thus, when the catheter is advanced or withdrawn, the motion of the conical tip is likely to cause damage to the vessel wall. The likelihood of damage to the vessel is greatest when the tip is moved towards the distal end, i.e. if the device is reinserted. One may avoid the latter problem by withdrawing the tip into the tube that initially carries it, but doing so adds to the complexity of the operation.

The present invention solves the above-described problems by providing a method and device which effectively and easily removes clots from blood vessels.

SUMMARY OF THE INVENTION

The present invention comprises a thrombectomy catheter which includes two constituent catheters, designated as a delivery catheter and a receiving catheter, the constituent catheters preferably being disposed in a coaxial arrangement. Both the delivery and receiving catheters have balloons located at their respective distal ends, and both catheters have appropriate lumens for inflating the balloons. The balloons are formed of a material which is molded such that they assume predetermined desired shapes when inflated, so as to aid in the removal of the clot. In particular, the balloon of the receiving catheter preferably defines a cup-shaped receptacle for receiving clot material. The delivery and receiving catheter can be moved longitudinally, i.e. along the length of a blood vessel, so that the distance between the balloons can be varied.

The method of the present invention includes the following essential steps. Using a guiding catheter, the thrombectomy catheter is advanced over a guide wire into the vessel, with both balloons deflated, until the receiving catheter is just proximal to the clot. The delivery catheter is then advanced until it has passed the clot. The balloons of both catheters are then inflated, so that they occupy substantially all of the cross-sectional area of the vessel. The delivery catheter is withdrawn, pulling the clot into the cup-shaped receptacle defined by the inflated balloon of the receiving catheter. The balloons are then partially deflated, and both catheters are withdrawn as a unit, while the clot is trapped between the two balloons. Several passes of the delivery catheter may be necessary for complete removal of the clot. To advance the delivery catheter again, one first deflates its balloon, advances the catheter, inflates the balloon, and withdraws the catheter as before.

Although the delivery and receiving catheters are arranged coaxially in the preferred embodiment, they can also be arranged side by side, or in a monorail configuration, within the scope of the invention.

The present invention therefore has the primary object of providing a method and device for removing clots from blood vessels.

The invention has the further object of simplifying the procedure of removing clots from blood vessels, and for performing the procedure more reliably and with reduced risk to a patient.

The invention has the further object of providing a method of removing clots, which method does not require substantial additional training for the physician.

The invention has the further object of providing a thrombectomy catheter which removes clots from blood vessels without damaging the vessel walls.

The reader skilled in the art will recognize other objects and advantages of the invention, from a reading of the following brief description of the drawings, the detailed description of the invention, and the appended claims.

DETAILED DESCRIPTION OF THE INVENTION

Figure 1:
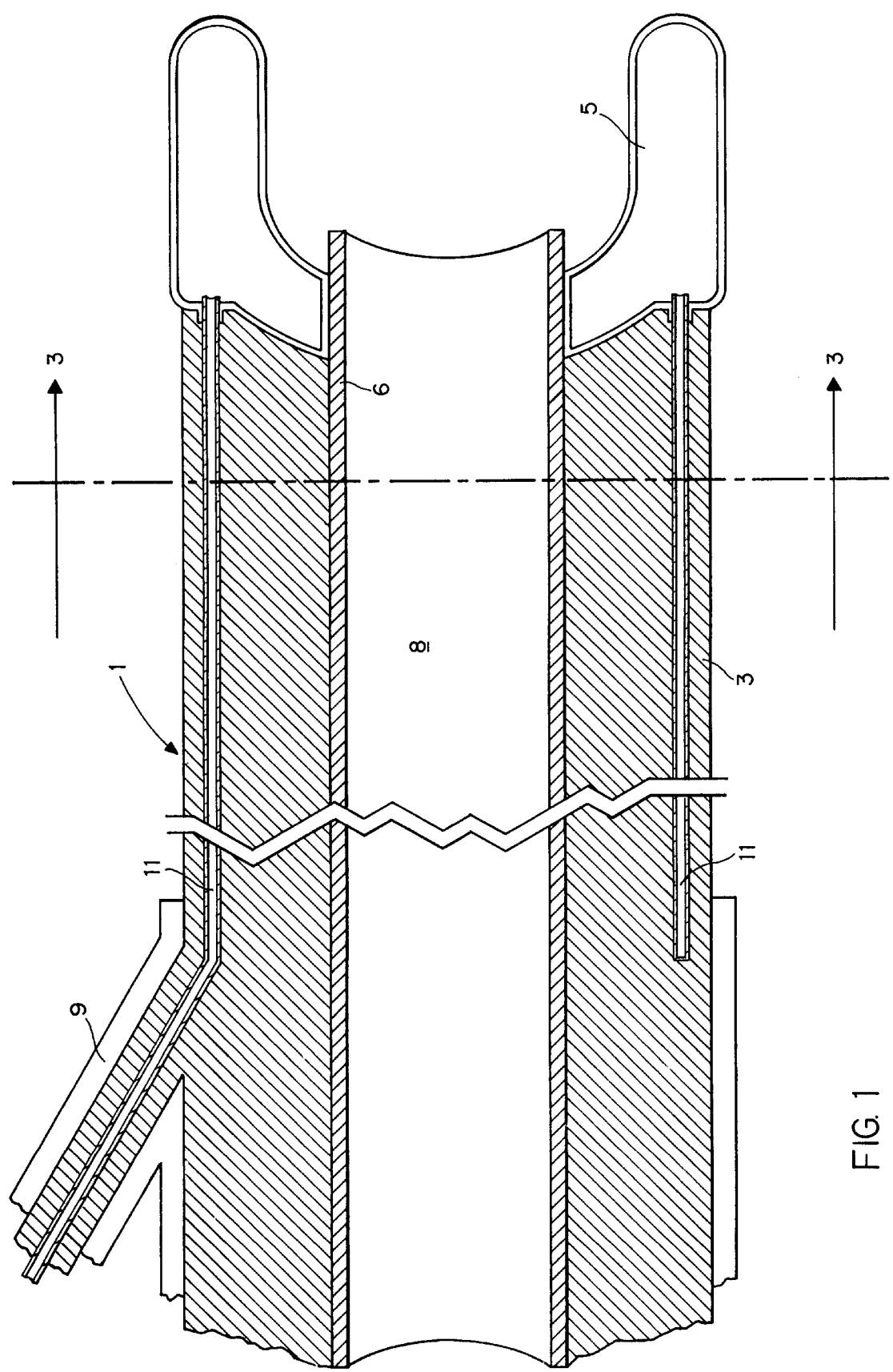
FIG. 1 provides a fragmentary cross-sectional view of the receiving catheter portion of the thrombectomy catheter of the present invention.

The present invention comprises a thrombectomy catheter which includes, as constituents, a receiving catheter and a delivery catheter. FIG. 1 shows the receiving catheter portion. Receiving catheter 1 includes catheter tube 3, and balloon 5 located at the distal end of the catheter tube. Interior tube 6 sits within tube 3, and defines interior lumen 8, which provides a passage large enough to accommodate the delivery catheter, described below. The interior tube may be integral with tube 3, or it may be formed separately and then bonded to the interior surface of tube 3.

The proximal end of the receiving catheter, shown in fragmentary form in the figure, is coupled to a "Y" touhy, the side port 9 of the touhy having an inflation lumen 11 which provides a fluid connection to balloon 5. In the embodiment of FIG. 1, the inflation lumen has an annular shape, but the lumen need not be annular, and many other arrangements of the lumen are possible, within the scope of the invention. For example, the inflation lumen could be eccentric, i.e. it could be a single cylindrical bore located at one radial position relative to the center of the tube. The invention should not be deemed limited by the shape of the inflation lumen.

Balloon 5 preferably has a toroidal shape, so that it can allow interior tube 6 to pass through it, as shown, without breaking the balloon. Other arrangements are possible. For example, balloon 5 could be formed of two halves, each half being a closed balloon, the two halves being firmly bonded to each other and together defining a ring. The invention is not limited by the specific construction of the balloons. What is important is that the catheter include an inflatable balloon which also allows a tube to pass through its middle without disturbing the balloon.

The balloon 5 is made of a material which can be molded so that it forms a predetermined shape when inflated. The technology necessary to form such balloons is commercially available. For example, balloons have been made, for use in cardiology, which balloons assume the shapes of sausages. In the present invention, the balloon is made such that when inflated it forms a cup or chalice which defines a reservoir or receptacle into which the thrombus can be deposited by the delivery catheter, as will be explained below. Since balloons that assume a desired shape when inflated have been known in the prior art, and are commercially available, the balloons, by themselves, do not form part of the present invention.

Preferably, the tip of the balloon has a platinum marker, to aid in positioning the balloon within the vessel.

Figure 2:
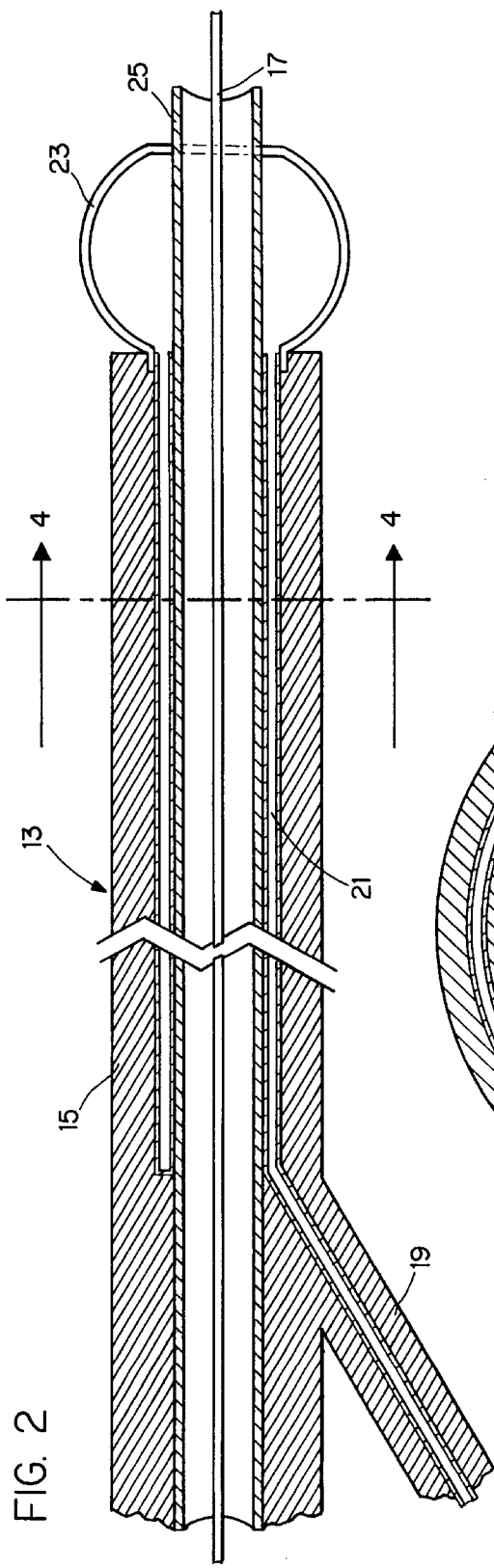
FIG. 2 provides a fragmentary cross-sectional view of the delivery catheter portion of the thrombectomy catheter of the present invention.

FIG. 2 shows the delivery catheter 13 made according to the present invention. The delivery catheter is designed to fit within interior lumen 8 of the receiving catheter. The delivery catheter is defined by catheter tube 15. The catheter is shown with guide wire 17. The guide wire sits within tube 25 which defines a lumen for the guide wire. In the embodiment shown, tube 25 protrudes beyond the balloon 23, and the balloon surrounds the tube. Side port 19 provides access to annular balloon lumen 21 which allows inflation of balloon 23.

Figure 4:
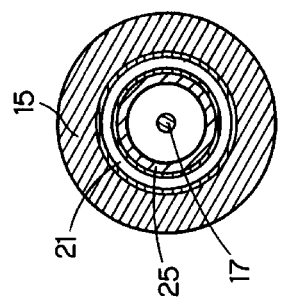
FIG. 4 provides a cross-sectional view, taken along the line 4—4 of FIG. 2.
Figure 3:
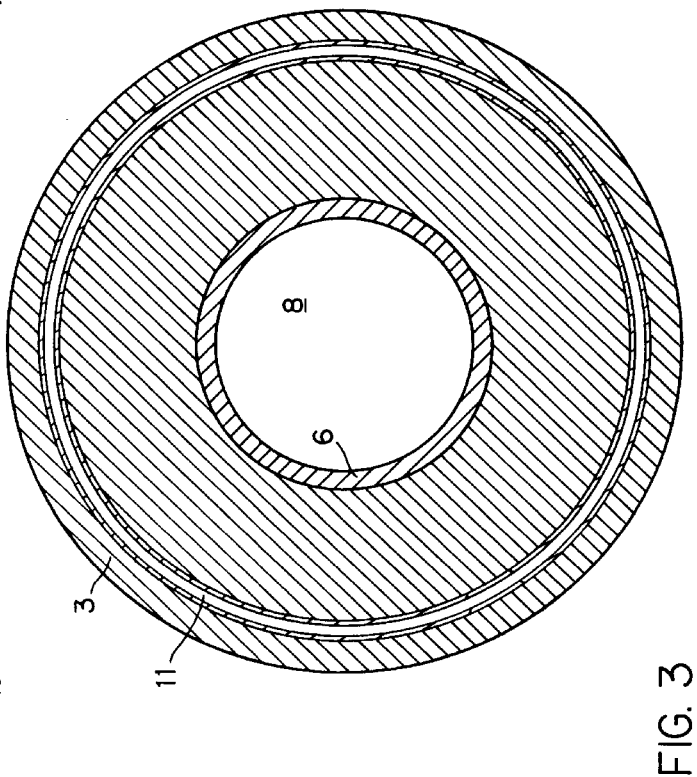
FIG. 3 provides a cross-sectional view, taken along the line 3—3 of FIG. 1.

FIGS. 3 and 4 provide further details of the cross-sections of the structures of FIGS. 1 and 2, respectively.

The balloon 23 of the delivery catheter is also molded so that it assumes a desired shape when inflated. For example, when inflated, the balloon may comprise a chalice, or it could be triangular, hemispherical, or sausage-shaped, according to the shape of the mold used to make it. Preferably, it should form a reservoir when inflated, with the reservoir portion on the proximal side. Thus, when the delivery catheter is withdrawn such that the two balloons touch, the balloons together define a receptacle which encases the clot material.

In other respects, the balloon is similar to the balloons currently used for angioplasty. Like the balloon for the receiving catheter, balloon 23 also may have a platinum marker at its tip.

In the preferred embodiment, the balloon of the delivery catheter is formed around and over a guide wire tube. But other arrangements could be used instead. The guide wire could be arranged side by side with the balloon, for example. All such arrangements are within the scope of the invention.

In one embodiment, the catheters and balloons may have the following dimensions. The receiving catheter may have an outside diameter of 7 French and an inside diameter of 5 French. The inflated outside diameter of balloon 5 can be about 3–5 mm. The delivery catheter may have an outside diameter of 3.5 French. The inflated outside diameter of balloon 23 can also be about 3–5 mm. The foregoing figures are given only as an example, and should not be deemed to limit the scope of the invention in any way. Other sizes can be used without departing from the scope of the present invention.

Figure 5A:
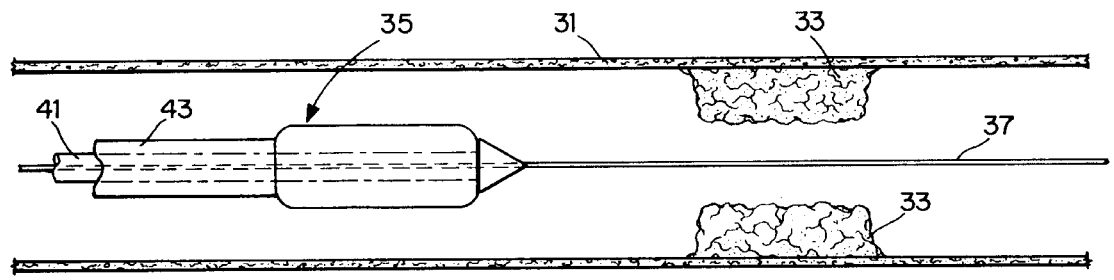
FIGS. 5a through 5f provide diagrams showing the method of using the thrombectomy catheter of the present invention.

FIGS. 5a through 5f illustrate the process of removing a clot, using the thrombectomy catheter of the present invention. FIG. 5a shows blood vessel 31 having clot 33 disposed around the inner wall of the vessel. The thrombectomy catheter 35, made according to the present invention, is threaded through the vessel, over guide wire 37. Before the thrombectomy catheter reaches the vicinity of the clot, the catheter is considered as one unit, although it comprises the separate receiving catheter 43 and delivery catheter 41.

FIG. 5a presupposes that the thrombectomy catheter has been properly introduced into the patient's body. The catheter is introduced into the body by a separate introducing catheter or guiding catheter, using conventional techniques. The introducing catheter forms no part of the present invention, and is therefore not illustrated.

Figure 5B:
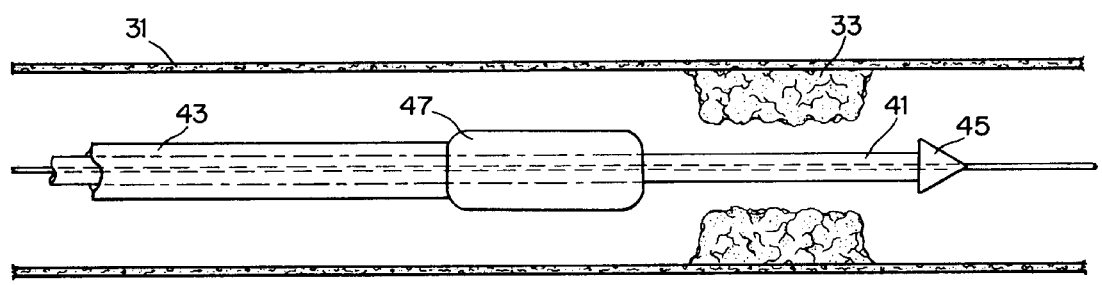

In FIG. 5b, the receiving catheter 43 has been stopped just short of the clot 33, so that the balloon 47 associated with the receiving catheter is immediately proximal to the clot. The delivery catheter 41 has been advanced so that its balloon 45 is immediately distal relative to the clot. Both balloons are still uninflated.

Figure 5C:
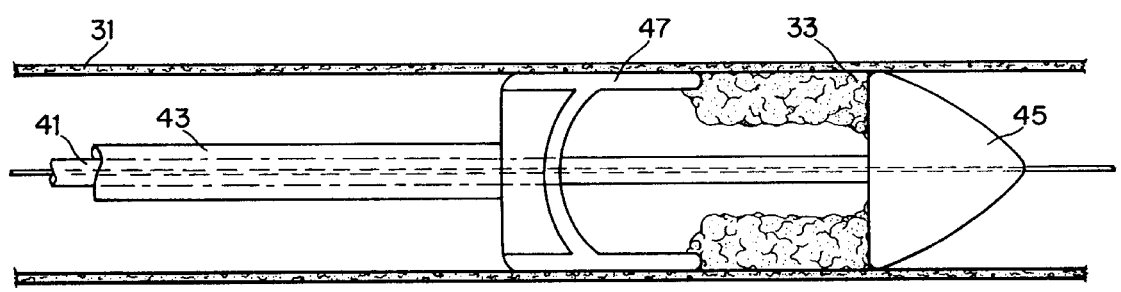

In FIG. 5c, both balloons have been inflated. Note that balloon 47 now defines a receptacle which is suited for collecting the clot material. The balloon 45 also defines an inside surface which complements the receptacle defined by balloon 47. The balloons completely surround the clot 33, and occupy substantially the entire cross-sectional area of vessel 31. Thus, the balloons extend to the interior wall of the vessel.

Figure 5D:
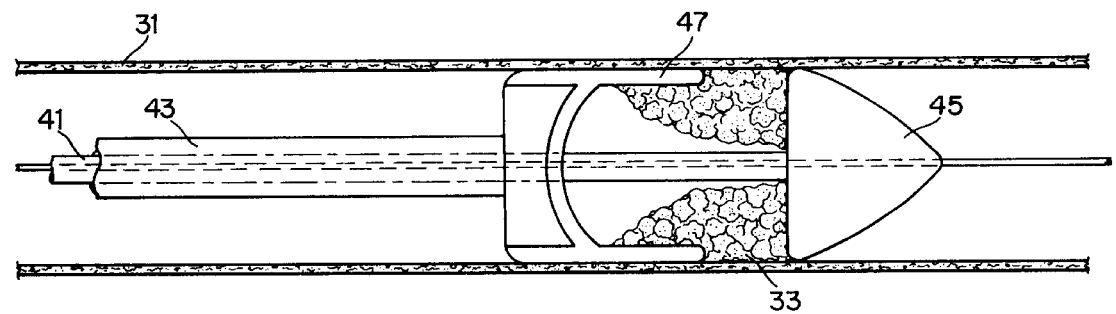

In FIG. 5d, the delivery catheter is being withdrawn, so that balloon 45 collects the clot material 33 from the wall of the vessel, and pushes this material towards balloon 47 of the receiving catheter.

Figure 5E:
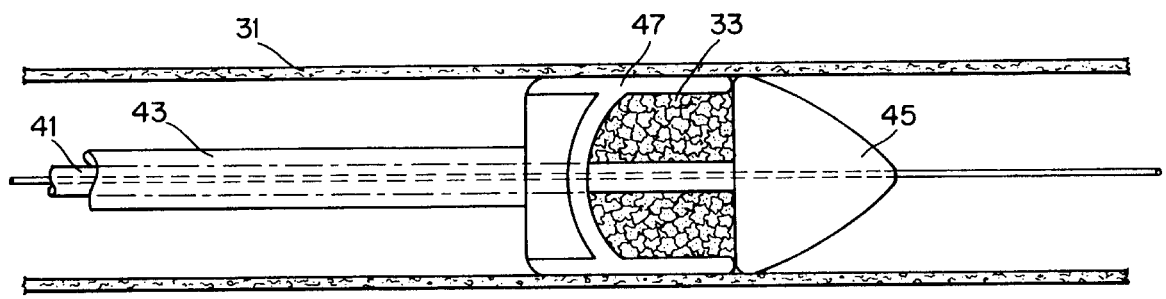

In FIG. 5e, the delivery catheter has been withdrawn by a distance sufficient to cause the proximal end of balloon 45 to contact the distal end of balloon 47. Clot material 33 is now completely encased within a cavity defined by the two balloons 45 and 47.

Figure 5F:
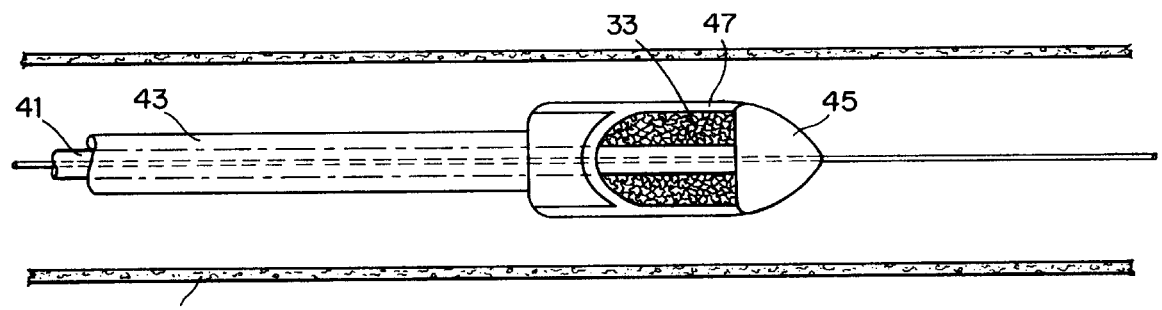

In FIG. 5f, the two balloons 45 and 47 have been partially deflated. The clot material 33 is thereby compressed, and is held firmly within the space defined by the two balloons. The thrombectomy catheter can now be withdrawn, as a unit, from the vessel, and the clot material can be discarded. Note that, due to the deflation of the two balloons, neither balloon is likely to scrape the wall of the vessel as the catheter is withdrawn.

An important advantage of the present invention is that the clot material is secured within the cavity defined by the two balloons. Thus, no clot material is likely to escape while the catheter is withdrawn. The present invention therefore virtually eliminates the risk of embolism due to the clot removal procedure.

If the above-described process does not suffice to remove all of the clot material in one attempt, part of the process can be repeated. After encasing some of the clot material in the space between the balloons, the delivery catheter is advanced again, in an at least partially deflated condition, to a position distal relative to the clot, and the balloon of the delivery catheter is re-inflated. The clot material previously removed from the vessel wall remains in the receptacle defined by balloon 47 of the receiving catheter, because it has been compressed by the two balloons. The delivery catheter is then withdrawn, so as to draw more clot material into the receptacle. The process can be repeated until all of the clot is collected in the receiving catheter. When all of the clot material has been removed, the balloons are deflated, and the catheter is removed.

Figure 6:
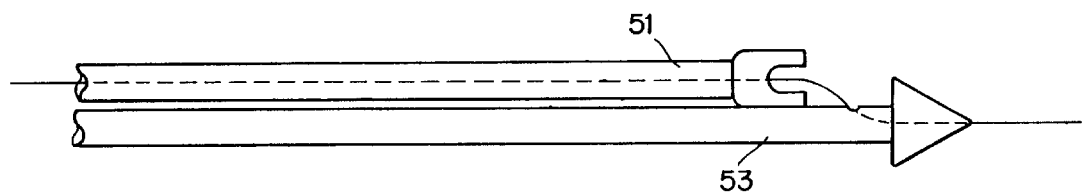
FIG. 6 provides a side elevational view of an alternative arrangement of the present invention, wherein the delivery and receiving catheters are disposed in a monorail configuration.
Figure 7:
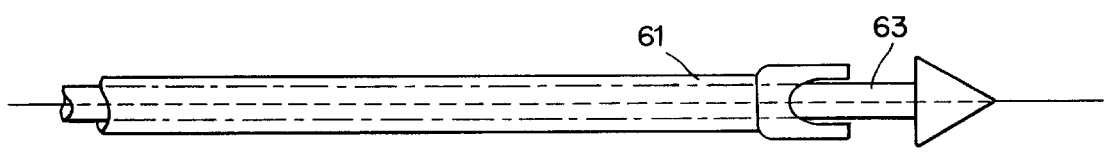
FIG. 7 provides a side elevational view of the preferred embodiment of the present invention, wherein the delivery and receiving catheters are disposed coaxially.
Figure 8:
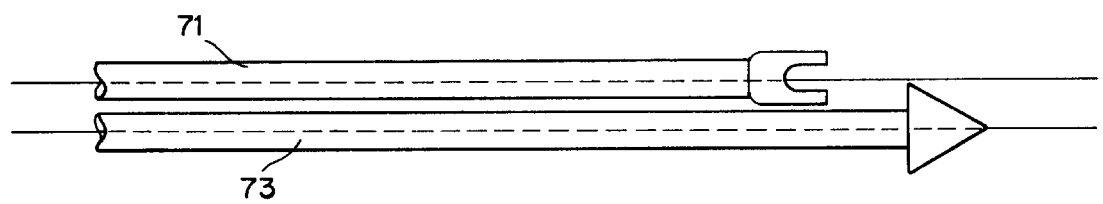
FIG. 8 provides a side elevational view of an alternative arrangement of the present invention, wherein the delivery and receiving catheters are disposed in a side by side configuration.

FIGS. 6–8 illustrate the three principal alternative arrangements of the receiving and delivery catheters, in the present invention. In FIG. 6, the receiving catheter 51 and the delivery catheter 53 are arranged in a "monorail" style, wherein the receiving catheter is threaded over a guide wire which passes out of the receiving catheter and into the distal end of the delivery catheter. In FIG. 7, the receiving catheter 61 and the delivery catheter 63 are arranged coaxially. The latter arrangement is what is shown in detail in FIGS. 1–5. In FIG. 8, the receiving catheter 71 and delivery catheter 73 are arranged side by side, each catheter being threaded over a separate guide wire. In all cases, the balloons function exactly as illustrated in FIGS. 5a through 5f.

The invention is not limited to the specific embodiments described above. The invention can be modified in various ways. The sizes and shapes of the delivery and receiving catheters can be varied. The placement and size of the inflation lumens can be changed. These and other modifications will be apparent to the reader skilled in the art, and should be considered within the spirit and scope of the following claims.

What is claimed is:

1. A method of removing a thrombus from a blood vessel, the method comprising the steps of:

a) advancing a two-part catheter to a position proximal to the thrombus, the two-part catheter including a delivery catheter and a receiving catheter, both the delivery catheter and the receiving catheters having distal ends, both the delivery catheter and the receiving catheter having balloons at their distal ends, the delivery catheter and receiving catheter being separable from each other, the balloon of the receiving catheter being permanently positioned at the distal end of the receiving catheter so that the balloon of the receiving catheter does not move longitudinally relative to the receiving catheter, b) advancing the delivery catheter to a position distal to the thrombus, c) inflating the balloons such that both balloons occupy substantially an entire cross-sectional area of the vessel, d) withdrawing the delivery catheter so as to pull the thrombus into the inflated balloon of the receiving catheter, wherein the thrombus is substantially encapsulated between the balloons of the delivery catheter and the receiving catheter, e) at least partially deflating the balloons, and f) removing the delivery catheter and the receiving catheter, with both balloons, from the vessel, the removing step being performed without inserting the delivery catheter and the receiving catheter into any other catheter.

2. The method of claim 1, wherein the step (f) is performed on both the delivery catheter and the receiving catheter as a unit.

3. The method of claim 1, wherein, after completion of step (e), steps (b) through (e) are performed at least one more time before step (f) is performed.

4. A method of removing clot material from a blood vessel, the method comprising the steps of:

a) surrounding the clot material by a pair of uninflated balloons, b) inflating the balloons, c) moving one of the balloons within the vessel towards the clot material and towards the other balloon, so as to dislodge the clot material from the vessel, and so as to encase at least some of the clot material between the balloons, d) at least partially deflating the balloons, and e) withdrawing the pair of balloons, with the encased clot material, from the vessel, wherein one of the balloons is connected to a receiving catheter and wherein another of the balloons is connected to a delivery catheter, the receiving catheter having a distal end, wherein the balloon of the receiving catheter is permanently positioned at the distal end of the receiving catheter so that the balloon of the receiving catheter does not move longitudinally relative to the receiving catheter, and wherein step (e) comprises the step of withdrawing the delivery catheter and the receiving catheter from the vessel, the withdrawing step being performed without inserting the delivery catheter and the receiving catheter into any other catheter.

5. The method of claim 4, wherein step (c) comprises the step of withdrawing the delivery catheter.

6. A device for removal of a thrombus in a vessel, the device comprising a delivery catheter and a receiving catheter, the delivery catheter and receiving catheters being provided as a unit but being separable from each other, both the delivery catheter and the receiving catheter having distal ends, the distal end of the delivery catheter having a balloon, the device including means for deflating the balloons, the balloon of the receiving catheter being permanently positioned at the distal end of the receiving catheter so that the balloon of the receiving catheter does not move longitudinally relative to the receiving catheter, wherein the balloon of the receiving catheter includes means for forming a cup-shaped receptacle when the balloon of the receiving catheter is inflated, and wherein the receiving catheter and the deflating means comprise means for withdrawing the balloon of the receiving catheter, from the vessel, without insertion of said balloon into any other catheter.

7. The device of claim 6, wherein the receiving catheter includes an interior lumen, and wherein the delivery catheter is inserted through and occupies the interior lumen of the receiving catheter.

8. The device of claim 6, wherein the receiving catheter and the delivery catheter both have at least one inflation lumen providing fluid paths to the balloons.

9. The device of claim 6, wherein the balloon of the receiving catheter and the balloon of the delivery catheter are arranged adjacent to each other.

10. The device of claim 6, wherein the delivery catheter and the receiving catheter are threaded over a single guide wire, and wherein the guide wire passes first through the receiving catheter, then out of the receiving catheter, and then into a distal end portion of the delivery catheter.

11. A device for removal of a thrombus in a vessel, the device comprising a delivery catheter and a receiving catheter, the delivery catheter being located inside and slidable relative to the receiving catheter, both catheters having distal ends, each catheter having a balloon at its distal end, the device including means for deflating the balloons, the balloon of the receiving catheter being permanently positioned at the distal end of the receiving catheter so that the balloon of the receiving catheter does not move longitudinally relative to the receiving catheter, wherein the balloon of the receiving catheter includes means for forming a cup-shaped receptacle when the balloon of the receiving catheter is inflated, and wherein the receiving catheter and the deflating means comprise means for withdrawing the balloon of the receiving catheter, from the vessel, without insertion of said balloon into any other catheter.

12. The device of claim 11, wherein the delivery catheter fits within an interior lumen formed inside the receiving catheter and wherein the delivery catheter is inserted through an occupies the interior lumen of the receiving catheter.

13. The device of claim 11, wherein the receiving catheter and the delivery catheter both have at least one inflation lumen providing fluid paths to the balloons.

14. The device of claim 11, wherein the balloon of the receiving catheter and the balloon of the delivery catheter are arranged adjacent to each other.

15. The device of claim 11, wherein the delivery catheter and the receiving catheter are threaded over a single guide wire, and wherein the guide wire passes first through the receiving catheter, then out of the receiving catheter, and then into a distal end portion of the delivery catheter.

16. A device for removal of a thrombus in a vessel, the device comprising a delivery catheter and a receiving catheter, the delivery catheter and receiving catheters being provided as a unit but being separable from each other, both the delivery catheter and the receiving catheter having distal ends, the distal end of the delivery catheter having a balloon, the distal end of the receiving catheter having a balloon, wherein the balloon of the receiving catheter includes means for forming a cup-shaped receptacle when the balloon of the receiving catheter is inflated, wherein the delivery catheter and the receiving catheter are threaded over a single guide wire, and wherein the guide wire passes first through the receiving catheter, then out of the receiving catheter, and then into a distal end portion of the delivery catheter.

17. A device for removal of a thrombus in a vessel, the device comprising a delivery catheter and a receiving catheter, the delivery catheter being located inside and slidable relative to the receiving catheter, both catheters having distal ends, each catheter having a balloon at its distal end, wherein the balloon of the receiving catheter includes means for forming a cup-shaped receptacle when the balloon of the receiving catheter is inflated, wherein the delivery catheter and the receiving catheter are threaded over a single guide wire, and wherein the guide wire passes first through the receiving catheter, then out of the receiving catheter, and then into a distal end portion of the delivery catheter.

* * * * *